United States Patent [19]

La Russa et al.

[11] 4,236,519

[45] Dec. 2, 1980

[54] CORNEAL PUNCH

[76] Inventors: Joseph A. La Russa, 451 Rutledge Dr., Yorktown Hgts., N.Y. 10598; Richard C. Troutman, 860 United Nations Plaza, New York, N.Y. 10021; Anthony R. Attler, 74 Price St., Dobbs Ferry, N.Y. 10522

[21] Appl. No.: 893,938

[22] Filed: Apr. 6, 1978

[51] Int. Cl.³ .................................. A61B 17/32
[52] U.S. Cl. ........................................ 128/305
[58] Field of Search ............. 128/305, 2 B, 310, 751, 128/754; 30/316

[56] References Cited

U.S. PATENT DOCUMENTS 493,730  3/1893  MacKenzie ..................... 128/310

*Primary Examiner*—Robert W. Michell
*Assistant Examiner*—Michael H. Thaler
*Attorney, Agent, or Firm*—Leonard Weiss

[57] ABSTRACT

A cylindrical sleeve has a conically tapered end from which three spring members extend. Additionally, within the sleeve is a shaft that has a portion which extends from the tapered end. The extending portion includes an end of the shaft in the shape of a right truncated cone. The spring members, the extending portion and the tapered end are all inserted within a hollow cylindrical blade that has a cutting edge at its distal end. An edge of the proximal end of the blade is maintained in contact with the tapered end by adjusting the length of the extending portion to cause the extending portion to push the spring members against the interior surface of the blade.

6 Claims, 6 Drawing Figures

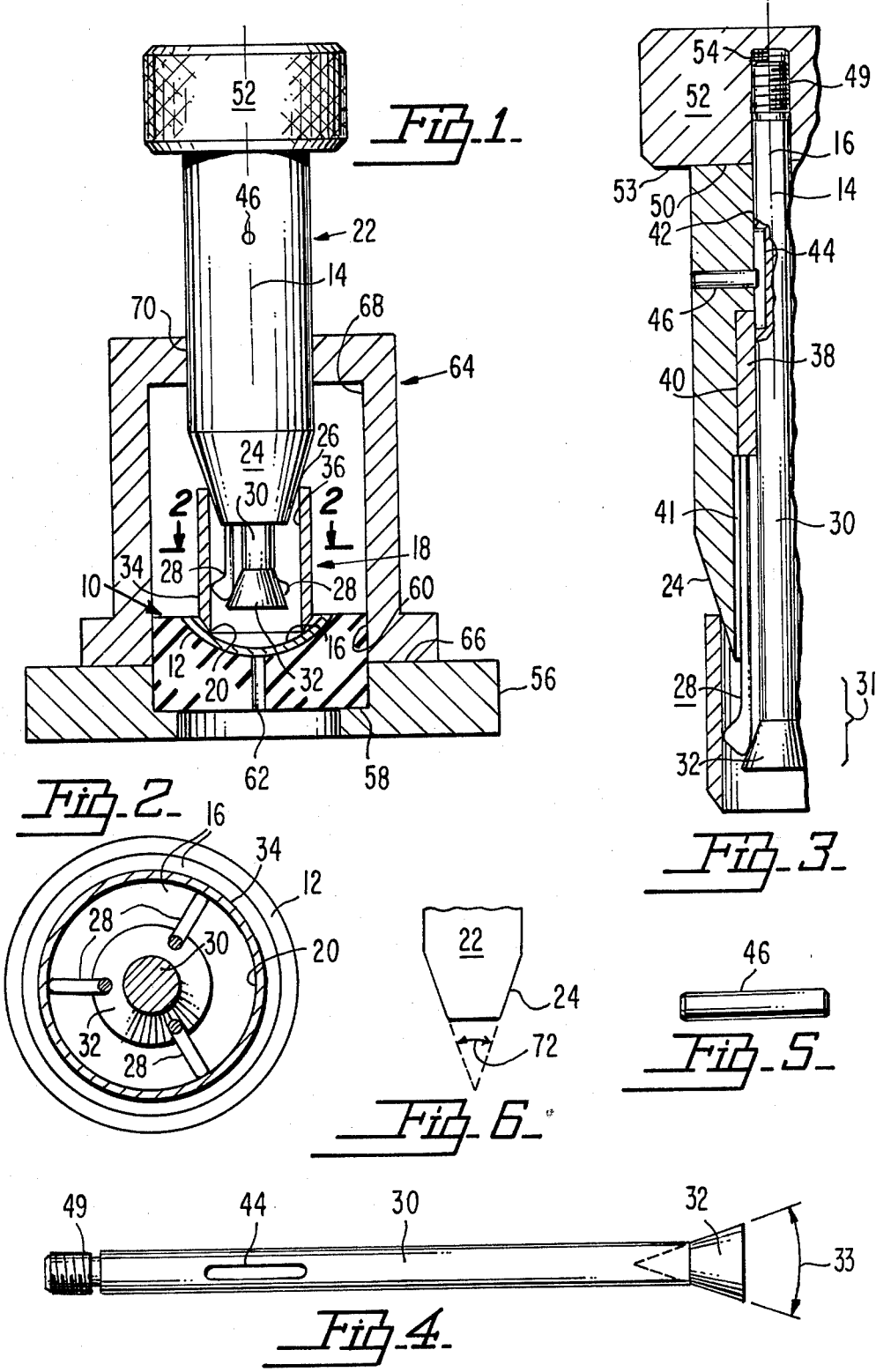

CORNEAL PUNCH

BACKGROUND OF THE INVENTION

1. Field of Invention

This invention relates to ophthalmic surgery and more particularly to cutting the cornea of an eye.

2. Description of the Prior Art

The cornea, the outer tissue of an eye, is frequently the subject matter of ophthalmic surgery. In a corneal transplant, for example, a central portion of the cornea of a patient's eye is surgically removed. Preferably, the surgical removal is by a cut that is parallel to the axis of the patient's eye. The surgical removal leaves a hole in the patient's eye that is circularly symmetric about the axis thereof.

The hole is filled by a central portion of the cornea of an eye of a donor. Analogous to the hole, the central portion of the donor's cornea is circularly symmetric about the axis of the donor's cornea. Moreover, when a cut of the donor's cornea is made to provide the central portion thereof, the cut is preferably parallel to the axis of the donor's cornea.

Usually, the cut of the donor's cornea is made in a cutting fixture by a hollow cylindrical blade that has a cutting edge at one end. The donor's cornea is placed upon a work surface of the fixture and the blade is advanced along its axis towards the donor's cornea, thereby bringing the cutting edge against the donor's cornea. Because the blade is cylindrical, the cut of the donor's cornea is circular.

It should be appreciated that the desired diameter of the cut of the donor's cornea is usually, if not always, in a range of six and one-half millimeters to eleven millimeters. Typically, the desired diameter of the cut of the donor's cornea is in a two millimeter range—a range of seven to nine millimeters.

When the fixture is suitable for use with a blade with a cutting edge of one diameter, it is usually not suitable for use with blades with cutting edges of other diameters. Additionally, a simplified fixture for maintaining the work surface in a desired space relationship to a cutting edge is unknown in the prior art.

SUMMARY OF THE INVENTION

According to the present invention, a plurality of spring members extends from a generally cylindrical sleeve that has an outer portion with a conical taper; said tapered portion and said spring members are adapted for insertion within a hollow cylindrical blade that has a cutting edge at its distal end; when said insertion causes the proximal end of said blade to be in contact with said tapered portion and said spring members are in contact with the interior of said blade, said tapered portion and said spring members maintain said blade and said sleeve in a coaxial relationship.

Objects, features and advantages of the present invention will become more apparent in the light of the following detailed description of a preferred embodiment thereof, as illustrated in the accompanying drawing.

BRIEF DESCRIPTION OF THE DRAWING

FIG. 1 is a side elevation with parts broken away, of the preferred embodiment of the present invention;

FIG. 2 is a view of the interior of a cylindrical blade in the embodiment of FIG. 1 taken along the line 2—2;

FIG. 3 is a view of a sleeve, with parts broken away, of the embodiment of FIG. 1;

FIG. 4 is a side elevation of a shaft in the embodiment of FIG. 1;

FIG. 5 is a perspective view of a key that maintains the shaft against rotation relative to the sleeve; and FIG. 6 is a side elevation of an end of the sleeve.

DESCRIPTION OF THE PREFERRED EMBODIMENT

In the preferred embodiment, the cornea of a donor's eye is cut by a cutting edge at the distal end of a cylindrical blade. The tapered end of a sleeve of a punch is inserted within the blade for contact with the proximal end of the blade. The contact maintains the blade and the sleeve in a coaxial relationship whereby an axial movement of the sleeve towards the cornea causes an axial movement of the blade towards the cornea. As explained hereinafter, the end of the sleeve is tapered to define a cone angle of 35 degrees, whereby the blade may be any of a plurality of suitable diameters.

As shown in FIG. 1, a teflon tray 10 has a double concave spherical work surface 12 with centers of curvature located upon a central axis 14 of the surface 12. The radius of curvature of most of surface 12 is approximtely eight millimeters. However, remote from the axis 14, the surface 12 has a radius of curvature of slightly less than eight millimeters. A cornea 16 of a donor's eye has its outer surface disposed upon the surface 12 with the center of the cornea 16 disposed substantially upon the center of the surface 12. Because of its double concave curvature, the surface 12 is suitable for placing the cornea 16 thereon without an undesirable buildup of folds.

A central portion of the cornea 16 is cut by a hollow cylindrical blade 18 that has a circular cutting edge at the distal end 20 thereof. The blade 18 is maintained in coaxial relationship with the axis 14 in a manner explained hereinafter. Because of the coaxial relationship, the blade 18 is operable to make a circular cut through the cornea 16. After the cut, the central portion of the cornea 16 is of a size suitable for surgical transplant into the eye of a patient.

To maintain the coaxial relationship, a substantially cylindrical sleeve 22 has a tapered end 24 that is inserted within the blade 18. The insertion brings substantially all of a circular section of the end 24 in contact with a circular edge 26 of the proximal end of the blade 18. Additionally, three spring members 28 extend from a central hole within the sleeve 22 at the end 24 to the interior of the blade 18. As best shown in FIG. 2, the members 28 have an equal angular distance therebetween about the axis 14.

As shown in FIGS. 3-5, a shaft 30, within the sleeve 22, has a portion 31 that extends from the central hole at the end 24. The extending portion 31 includes one end 32 of the shaft 30 that has a shape of a right truncated cone. Preferably, end 32 defines a cone angle 33 of approximately 65 degrees. It should be understood that the shaft 30 is coaxial with the axis 14. As explained hereinafter, the shaft 30 is operable to be moved axially into the sleeve 22 to cause the end 32 to bear against the members 28 whereby teeth 34 at the ends of members 28 are pushed against an interior surface 36 of the blade 18. The teeth 34 maintain the circular section of the end 24 in contact with all of the edge 26. When the circular section of the end 24 is in contact with all of the edge 26, the blade 18 is locked and positively aligned in the coaxial relationship with the axis 14.

Within the sleeve 22 (FIG. 3), the members 28 are all integral with a cylindrical tube 38 which is in slideable contact with the shaft 30 and fixedly connected within a first recess 40 of the sleeve 22. The members 28 extend from the tube 38 through a second recess 41 which is contiguous with the central hole at the end 24.

The shaft 30 is additionally in slideable contact with an interior bearing surface 42 of the sleeve 22. Preferably, the shaft 30 has a keyway 44 that receives one end of a key 46 (FIG. 5) that has a shape of a cylindrical rod. The key 46 extends through a hole 48 (FIG. 1) within the sleeve 22 whereby the shaft 30 is maintained against axial rotation relative to the sleeve 22. From the description given hereinbefore, the shaft 30 may be made to slide axially to cause the extending portion 31 to be of a desired length. Moreover, the range of the sliding of the shaft 30 is substantially equal to the length of the keyway 44.

The shaft 30 has a threaded end 49 (FIGS. 3 and 4) that extends through an end 50 of the sleeve 22. Moreover, a knurled knob 52 has a central hole 54 with threads that engage the threaded end 49.

In this embodiment, a bottom surface 53 of the knob 52 is held in an abutting relationship to the end 50 because the end 32 bears against the teeth 34. When the knob 52 is rotated clockwise relative to the sleeve 22, the threaded end 49 is forced into the hole 54 because the shaft 30 is maintained against rotation. When the threaded end 49 is forced into the hole 54, the shaft 30 slides in a direction that decreases the length of the extending portion 31. Correspondingly, when the knob 50 is rotated counter clockwise relative to the sleeve 22, the threaded end 49 is forced out of the hole 54, thereby causing the shaft 30 to slide in a direction that increases the length of the extending portion 31. Because the length of the extending portion 31 can be either decreased or increased, the extending portion 31 is operable to cause the teeth 34 to bear against the interior surface 36 when the blade 18 is of any of a plurality of diameters.

As shown in FIG. 1, the tray 10, referred to hereinbefore, has a lower portion maintained within a cylindrical base 56 upon a shoulder 58 thereof. Moreover, there is a force fit between an interior surface 60 of the base 56 and the tray 10, thereby preventing movement between the tray 10 and the base 56. Preferably, the tray 10 has a central hole 62 that inhibits a formation of an air bubble between the cornea 16 and the surface 12.

An upper portion of the tray 10 is maintained within a hollow guide 64 that has a bottom surface 66 that abuts the top of the base 56. Moreover, there is a force fit between an interior surface 68 of the guide 64 and the tray 10.

The guide 64 has an interior surface 70 that is in slideable contact with the sleeve 22. Because of the slideable contact and because of the force fit between the tray 10 and the interior surface 68, the tray 10 and the sleeve 22 are maintained in a coaxial relationship with the axis 14. Therefore, the blade 18 is moved axially when the sleeve 22 slides in the guide 64.

As shown in FIG. 6, the end 24 preferably defines an angle 72 of approximately 35 degrees. Applicant has found that when the angle 72 is approximately 35 degrees and the angle 33 is approximately 65 degrees (as described hereinbefore), the corneal punch may be used with blades with cutting edges that have diameters that differ by as much as two millimeters.

A surgical instrument for cutting a hole in a patient's eye is provided in an alternative embodiment that utilizes all elements of the preferred embodiment except the tray 10, the base 56 and the guide 64.

Thus, there has been shown and described a corneal punch in accordancce with the invention. However, although shown and described with respect to a preferred embodiment thereof, it should be understood by those skilled in the art that various changes and omissions in the form and detail may be made in the present invention without departure therefrom.

Having thus described a typical embodiment of our invention, that which we claim as new and desire to secure by Letters Patent of the United States is:

1. A corneal punch for cutting a portion of the cornea of an eye, comprising:

a sleeve with an outer portion that has a conical taper, said sleeve being adapted for insertion within a hollow cylindrical blade that has a cutting edge at its distal end, said insertion causing the proximal end of said blade to contact said tapered portion along a circle;

a plurality of radially adjustable spring members that extends from a central hole at an end of said sleeve; and a shaft within said sleeve that has a portion that extends from said central hole, said extending portion having the shape of a right truncated cone that pushes said members into contact with the interior surface of said blade.

2. The corneal punch of claim 1 wherein said members are three in number and have equal angular spacing about the axis of said sleeve.

3. The corneal punch of claim 1 wherein said conical tapered portion is at said end of said sleeve.

4. The corneal punch of claim 1 wherein said conical tapered portion and said right truncated cone define angles of approxiamtely 35 degrees and 65 degrees, respectively.

5. The corneal punch of claim 1 additionally comprising means for adjusting the length of said extending portion.

6. A corneal punch for cutting a portion of the cornea of an eye, comprising:

a sleeve with an outer portion that has a conical taper, said sleeve being adapted for insertion within a hollow cylindrical blade that has a cutting edge at its distal end, said insertion causing the proximal end of said blade to contact said tapered portion along a circle;

a plurality of radially adjustable spring members that extends from a central hole at an end of said sleeve;

means connected to said sleeve for maintaining said spring members in contact with an interior surface of said blade;

a work surface having a concave shape; and means for maintaining said sleeve in a coaxial relationship with said work surface.

* * * * *